US008609083B1

(12) United States Patent
Shapiro-Ilan et al.

(10) Patent No.: US 8,609,083 B1
(45) Date of Patent: Dec. 17, 2013

(54) METHOD FOR CONTROLLING FUNGAL PATHOGEN WITH BACTERIAL METABOLITE

(75) Inventors: David I. Shapiro-Ilan, Macon, GA (US); Charles C. Reilly, Warner Robins, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1462 days.

(21) Appl. No.: 11/726,745

(22) Filed: Mar. 22, 2007

(51) Int. Cl.
*A01N 63/02* (2006.01)
*A01N 63/00* (2006.01)

(52) U.S. Cl.
USPC .................. 424/93.4; 435/252.1; 424/117

(58) Field of Classification Search
None
See application file for complete search history.

(56) References Cited

U.S. PATENT DOCUMENTS 5,569,668 A * 10/1996 Webster et al. ............... 514/419

FOREIGN PATENT DOCUMENTS

WO    WO 95/03695    2/1995

OTHER PUBLICATIONS

Chen et al., Journal of Invertebrate Pathology 68, 101-108 (1996).*
Chen, G., G. Dunphy and J.M. Webster, Antifungal Activity of Two *Xenorhabdus* Species and *Photorhabdus luminescens*, Bacteria Associated with the *Nematodes steinernema* Species and *Heterorhabditis megidis*., Biological Control 4:157 (1994)).*
Vyas et al., International Arachis Newsletter (IAN), 2005.*

* cited by examiner

*Primary Examiner* — Irene Marx
(74) *Attorney, Agent, or Firm* — John Eado; Albert Y. Tsui; Lesley Shaw

(57) ABSTRACT

This invention relates to using bacterial metabolites to suppress phytopathogens, more particularly this invention relates to bacterial metabolites applied to *Carya illinoensis* and *Prunus persica* as a fungicide to suppress and inhibit *Glomerella cingulata*, *Phomopsis* sp., *Phytophthora cactorum*, *Fusicladosporium effusum*, and *Monilinia fructicola*.

5 Claims, 14 Drawing Sheets

*F. effusum*

FIG. 1E

METHOD FOR CONTROLLING FUNGAL PATHOGEN WITH BACTERIAL METABOLITE

BACKGROUND OF THE INVENTION

Figure 1A:
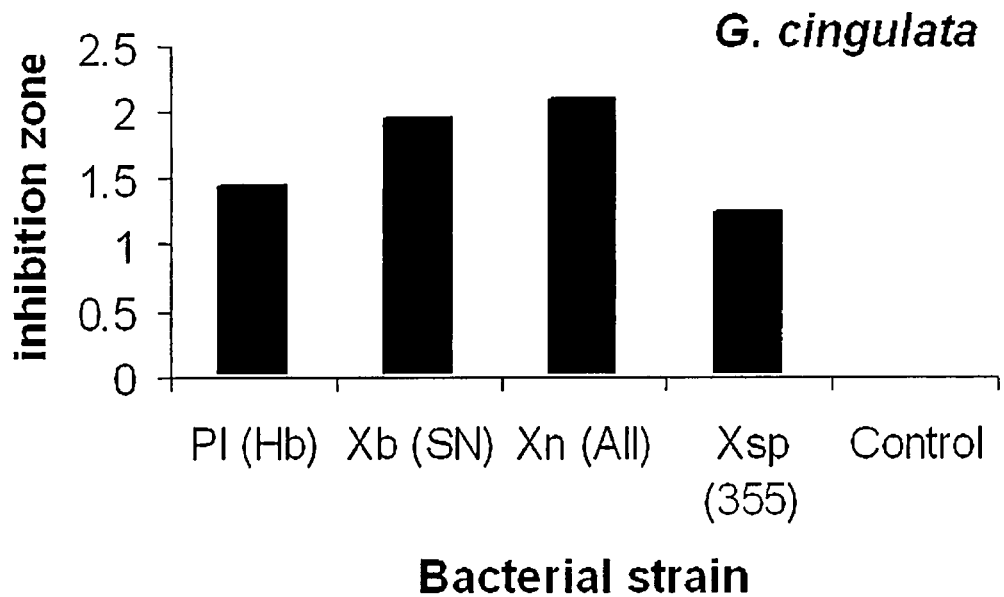
Figure 1B:
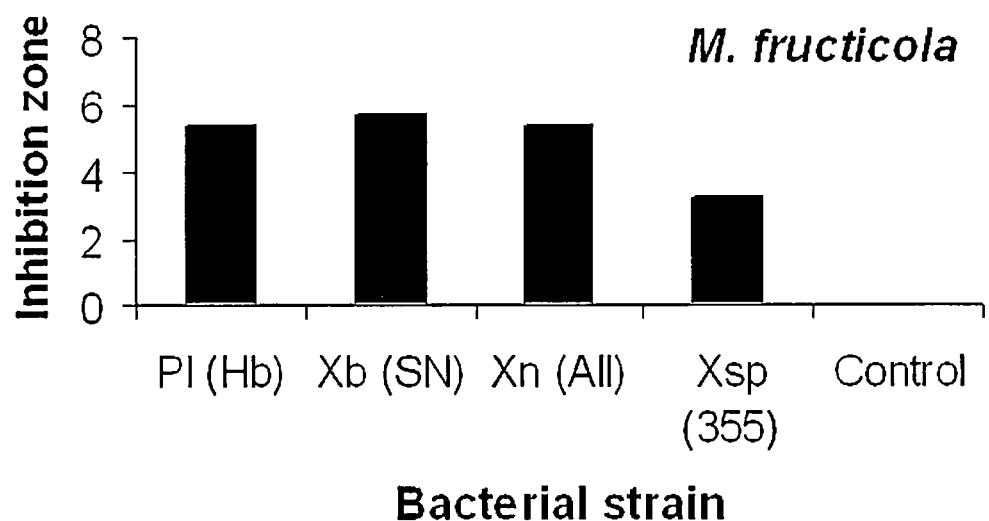
Figure 1C:
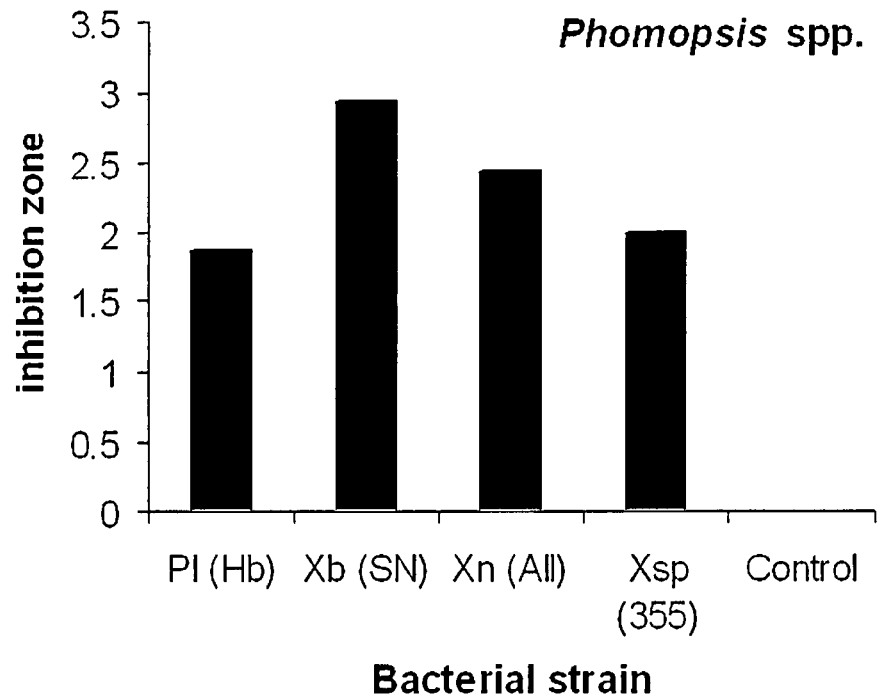
Figure 1D:
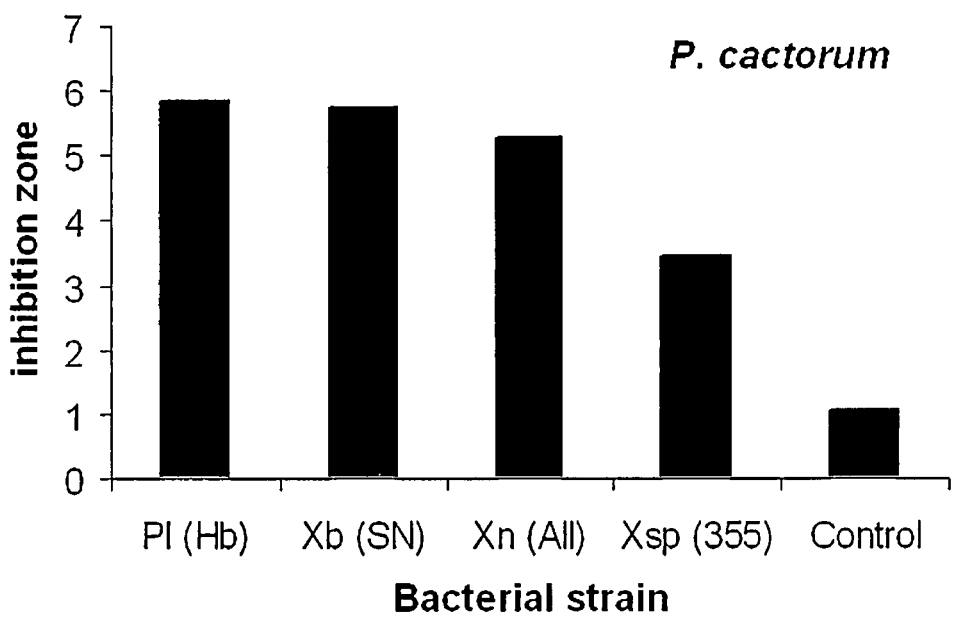

Fungicides are compounds of natural or synthetic origin that protect plants against damage caused by fungi. Current methods of agriculture rely heavily on the use of fungicides. In fact, some crops cannot be grown usefully without the use of fungicides. Using fungicides allows a grower to increase the yield of the crop and consequently, increase the value of the crop. Many synthetic fungicides are classified as carcinogens by the Environmental Protection Agency (EPA) and are toxic to wildlife and other non-target species. In addition, chemical fungicides are harmful towards vertebrates (humans), persist in the soil environment, and can contaminate ground water supply. Furthermore, prolong chemical fungicide application results in target-surviving fungi developing an evolutionary resistance to the chemical fungicide. In order to eradicate chemical resistant-fungi, a cycle of even more potent chemical fungicides are utilized, resulting in more environmental damage and eventually even more chemical resistant fungi.

Among pecans, peaches, and other fruit and nut trees, fungal and oomycete incited diseases are a significant concern for commercial productivity. In Southeastern parts of the United States, pathogens including, but not limited to *Glomerella cingulata*, *Phomopsis* spp., *Phytophthora cactorum*, and *Fusicladosporium effusum* have a substantial impact on pecan production. *Phytophthora* species are homothallic oomycetes which produce oospores that spread by rain splash or irrigation water. *Glomerella*, *Phomopsis*, and *Fusicladosporium* species produce conidia or ascospores that spread by rain splash or wind. The fungus *Monilinia fructicola* also has a substantial impact on peach production.

Fungal pathogens such as *Glomerella cingulata*, *Phomopsis* sp., *Phytophthora cactorum*, *Fusicladosporium effusum*, and *Monilinia fructicola* are controlled by chemical fungicides such as dodine, fenbuconazole, and triphenyltin hydroxide. However, environmental concerns, toxicological effects, and concern over target-organism resistance warrants development of alternative control methods. Methods for biocontrol via bacteria biotoxins have been recognized. For example, see Smart, G. C. (1995) "Entomopathogenic Nematodes for the Biological Control of Insects", Journal of Nematology (Supplement) 27(4S):529-534, U.S. Pat. Nos. 6,048,838, and 5,549,889.

Insect pathogenic nematodes of the families Steinernematidae and Heterorhabditidae are symbiotically associated with bacteria of the genera *Xenorhabdus* and *Photorhabdus* respectively. The entomopathogenic nematodes generally form enduring juveniles that are adapted for long-term survival in soil conditions. The symbiotic bacteria are released into the haemolymph after penetration of the juvenile into a suitable insect host. The nematodes provide shelter to the bacteria, which, in return, kill the insect host and provide nutrients to the nematode. Symbiotic bacterial cannot survive in nature without the nematode, but can survive in sterile in vitro culture without the nematode host. Through various extraction methods, it has been observed that these nematode bacteria have the ability to kill a wide range of different insects without the aid of their nematode partners. While nematodes are used commercially on a wide range of insects, it is the endogenous symbiotic bacteria that are central to nematode virulence. The bacterial produced toxins and antibiotics are lethal towards insects, microbes and a variety of fungi.

Bacterial toxins, such as antibiotics, have been used to control pathogens. The toxin can be isolated and applied directly to the plant or the bacterial species may be administered so it produces the toxin in situ. It has been long known that bacteria and bacterial metabolites that have antimicrobial properties have been investigated for suppression of insect population, as elaborated by Smart, G. C. (1995) "Entomopathogenic Nematodes for the Biological Control of Insects", Journal of Nematology (Supplement) 27(4S):529-534.

*Xenorhabdus* spp. are symbionts of entomopathogenic *Steinernema* spp. nematodes, while *Photorhabdus* spp. are associated with *Heterorhabditis* spp. In nature, the bacteria exists in the intestine of their nematode symbionts or in the insect hosts that nematodes infect; the bacteria require the protection of the nematode to survive in the external environment. Given such bacteria are toxic to insects, it is well known in the art that bacterial produced toxins can be utilized as insecticides. For instance, U.S. Pat. No. 6,048,838 discloses a protein toxin isolated from *Xenorhabdus* strains as an insecticides. It is known in the art that *Xenorhabdus* spp. and *Photorhabdus* spp. metabolites with antibiotic activity can be cultured in vitro on solid media or in liquid fermentation. For instance see Paul V. J. et al., (1980) "*Antibiotics in microbial ecology*" Journal of Chemical Ecology 7:589-597, Barbercheck M. E. et al., (1996) "*Effect of Cucurbitacin D on in Vitro Growth of Xenorhabdus and Photorhabdus spp., Symbiotic Bacteria of Entomopathogenic Nematodes*" Journal of Invertebrate Pathology 68(2):141-145, U.S. Pat. No. 6,316,476, and WO 95/03695.

Chemical secondary metabolites from symbiotic bacteria have been identified. Specifically chemical groups of *Xenorhabdins*, *Xenorxides*, *Xenocoumacins*, *Indoles*, *Nematophics*, *Hydroxystilbenes*, and *Puromycins* derived from *Xenorhabdus* and *Photohabdus*. Indeed, some antimicrobial compositions, such as xenorxides and nematophin, have been identified as outlined in U.S. Pat. Nos. 6,316,476 and 5,569,668 respectively.

Although *Xenorhabdus* spp. and *Photorhabdus* spp. and their metabolites have been tested for suppression of some fungal or oomycete species pathogens such as, *Phytophthora infestans*, no tests have determined the potency of these agents against specific phytopathogens of pecan and peach plants. Fungicidal properties associated with these symbionts are known to vary among bacterial species and strain. Additionally, potency of bacterial metabolites from *P. luminescens* (VS), *Photorhabdus* sp. (MX4), and *Xenorhabdus* sp. (3-8b), have not been assessed for antibiotic activity against any organism, and the nematodes/bacteria complexes from which these metabolites were derived remain relatively unstudied. Thus, there is a need in the art to determine whether metabolites from *Xenorhabdus* and *Photorhabdus* species would be effective fungicide to protect peach and pecan crop from fungi such as *Glomerella cingulata*, *Phomopsis* sp., *Phytophthora cactorum*, *Fusicladosporium effusum*, and *Monilinia fructicola*.

In addition, there is a need to determine whether the bacterial metabolites of *Xenorhabdus* and *Photorhabdus* genera has any phytotoxicity throughout in vivo experimentation to determine whether any fungal suppressive effects are limited to only in vitro conditions.

BRIEF SUMMARY OF THE INVENTION

It is an object of this invention to provide a method of treating and suppressing fungal pathogen formation on orchard trees that overcomes the disadvantages of the prior art, resulting in increasing agricultural output.

It is one aspect of the invention to suppress fungi on peach and pecans trees using bacterial metabolites of *Photorhabdus* and *Xenorhabdus* spp. that are safe for humans and vertebrates. Adoption of the biological based control method would halt reliance on synthetic chemicals that is potentially harmful to vertebrates and the environment.

Another aspect of the invention is that fungal suppression is accomplished via liquid culture broth from metabolites of *Xenorhabdus* sp. and *Photorhabdus* sp. such that the metabolites are a biotoxin that is an effective fungicide. The biotoxin suppresses scab sporulation at levels equal to commonly used chemical fungicides.

Another aspect of the invention is that pecan crop production and peach crop production are protected from fungal pathogens such that the metabolites are applied to lesions to prevent sporulation. Unlike chemical based applications, the metabolite application will prevent lesion formation. Furthermore, the metabolic solution is minimally phytotoxic towards the pecan and peach plant. Furthermore, *Xenorhabdus* metabolites substantially suppressed *F. effusum* sporulation at levels greater than or equal to commercially used chemical fungicides.

Yet another aspect of the invention is that the metabolite is effective in orchards to suppress fungal pathogens that target peach and pecan trees. The metabolite suppresses pathogens such as *Glomerella cingulata, Phomopsis* sp., *P. cactorum, F. effusum*, and *M. fructicola*. It is another aspect of the invention is that *Photorhabdus* and *Xenorhabdus* metabolites be applied to soil in the spring to reduce the potential for *P. cactorum* infection.

It is another aspect of the invention that the metabolites can be applied to field plants to prevent sporulation such that the metabolite reduces *F. effusum* lesions already established. This is advantageous inasmuch as some chemical agents, such as triphenyltin, do not suppress or eradicate establish lesions.

Briefly, disclosed is a method for applying a fungicide on a plant, said method comprising identifying the plant in need of pathogen control, culturing nematode bacteria and collecting the bacterial metabolite; and contacting said plant with an effective amount of bacterial metabolite, whereby any pathogen on said plant is controlled.

Also, disclosed is a method for treating a fungal pathogen in a plant comprising, identifying a plant infected by a fungal pathogen, applying a composition having bacterial metabolites to said plant or portions thereof, whereby said composition results in said pathogen being controlled or eradicated.

Another aspect of the invention is that a probiotic composition comprising metabolite of at least one bacterium is selected from the group consisting of *P. luminescens, X. bovienii, X. nematophila, Xenorhabdus* sp., and *Photorhabdus* sp.

Consequently, there is a need to produce fungicides that are safer, that have better performance, that are easier to use, and that are cost effective. In light of the foregoing, the inventors provide this invention.

BRIEF DESCRIPTION OF THE DRAWING

The present invention together with the above and other objects and advantages may best be understood from the following detailed description of the embodiment of the invention illustrated in the drawings, wherein:

Figure 1E:
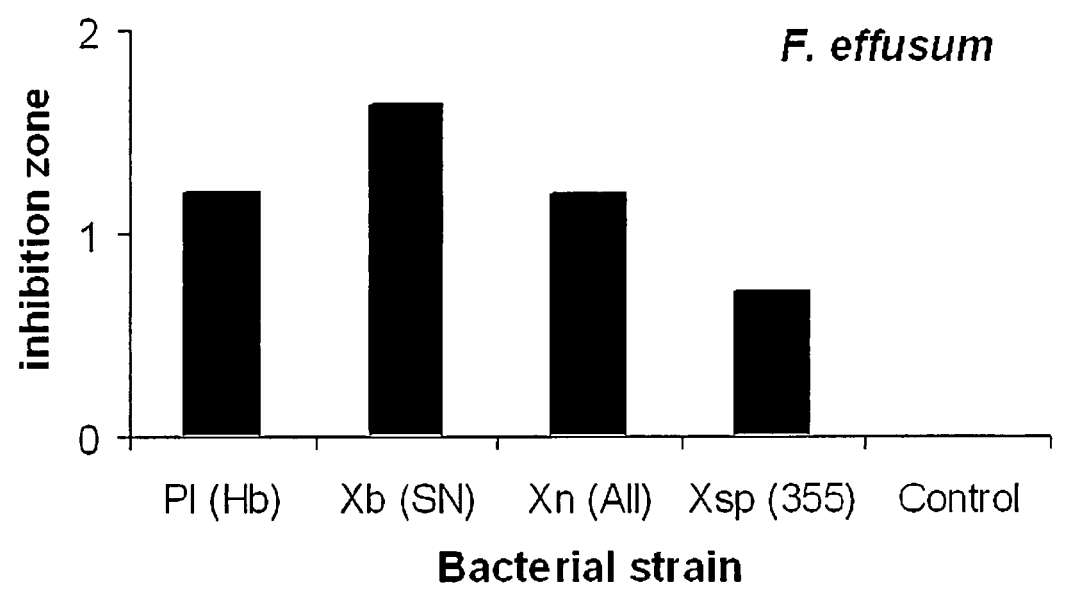

FIGS. 1A-E are graphs depicting a mean zone of inhibition ($cm^2$) caused by various bacterial metabolites from *Photorhabdus luminescens* (Hb), *Xenorhabdus bovienii* (SN), *Xenorhabdus nematophila* (All), and *Xenorhabdus* sp. (355) as applied to a plurality of pathogens;

FIGS. 2A-E are graphs depicting a mean zone of inhibition ($cm^2$) caused by various bacterial metabolites from *Photorhabdus luminescens* (Hb), *Photorhabdus luminescens* (VS), *Photorhabdus* sp. (MX4), *Xenorhabdus bovienii* (SN), and *Xenorhabdus* sp. (3-8b) as applied to a plurality of pathogens;

FIG. 3 is a graph depicting average number of spores per scab lesion produced by *Fusicladosporium effusum* based on various fungicidal treatments on pecan twig-buds. Treatments include chemical fungicides dodine, fenbuconazole (F), triphenyltin hydroxide (TH), and bacterial metabolites *Xenorhabdus bovienii* (SN strain) (Xb) and *Photorhabdus luminescens* (Hb strain) (Pl);

FIG. 4A is a graph depicting phytotoxicity levels of diluted bacterial metabolites derived from *Xenorhabdus bovienii* (SN strain) (Xb) and *Photorhabdus luminescens* (Hb strain) (Pl) on young (½ to ¾ expanded) detached pecan leaves;

FIG. 4B is a graph depicting phytotoxicity levels of diluted bacterial metabolites derived from *Xenorhabdus bovienii* (SN strain) (Xb) and *Photorhabdus luminescens* (Hb strain) (Pl) on mature (fully expanded and hardened) detached pecan leaves;

FIG. 5 is a graph depicting size ($cm^2$) of *Phytophthora cactorum* lesions on detached pecan leaves treated with diluted bacterial metabolites or an acetone or water control, in accordance with the features of the present invention.

FIGS. 6A-B are photographs of a pecan leaf with *Phytophthora cactorum* infection originating from an agar plug. FIG. 6A was sprayed with a water control, whereas FIG. 6B was sprayed with 12.5% *Photorhabdus luminescens* (Hb) metabolites.

DETAILED DESCRIPTION OF THE INVENTION

Deposited Organisms

A plurality of *Xenorhabdus* and *Photorhabdus* strains in accordance with the invention has been deposited under the Budapest Treaty in the National Center for Agricultural Utilization Research—Agricultural Research Service Culture Collection located at 1815 N. University Street, Peoria, Ill. on Feb. 28, 2007. Specifically, *Xenorhabdus nematophila* (All strain) has been assigned Deposit No. NRRL B-50006. *Photorhabdus luminescens* (VS strain) has been assigned Deposit No. NRRL B-50007. *Xenorhabdus* sp. (355 strain) has been assigned Deposit No. NRRL B-50008. *Photorhabdus luminescens* (Hb strain) has been assigned Deposit No. NRRL B-50009. *Xenorhabdus bovienii* (SN strain) has been assigned Deposit No. NRRL B-50010. *Xenorhabdus* sp. (3-8b strain) has been assigned Deposit No. NRRL B-50011. *Photorhabdus* sp. (MX4 strain) has been assigned Deposit No. NRRL B-50012.

DEFINITIONS

As used in the specification and claims, the singular form "a", "an" and "the" include plural references unless the context clearly dictates otherwise. For example, the term "a cell" includes a plurality of cells, including mixtures thereof.

As used herein, "biological control" is defined as control of a pathogen, insect, plant, or fungi by the use of a second biological organism. The second organism can entail parasites, predators or pathogens that results in the desired controlled organism population density to be at a lower average than would occur in the absence of the biological control organism. As an example, one such means of biological control is reducing fungi on plants with the application of bacterial metabolite biotoxin, wherein the bacteria is derived from nematodes.

The term "fungus" or "fungi" includes a wide variety of nucleated spore-bearing organisms that are devoid of chlorophyll. Examples of fungi include yeast, molds, mildews, rusts, and mushrooms. Specific genus of fungi includes *Glomerella, Phomopsis, Phytophthora*, and *Fusicladosporium.*

The term "bacteria" includes any prokaryotic organism that does not have a distinct nucleus. Examples of bacteria include, but are not limited to species such as: *Photorhabdus luminescens, Xenorhabdus bovienii*, or *Xenorhabdus nematophila.*

"Fungicidal" means the ability of a substance to increase mortality or inhibit the growth rate of fungi.

"Antifungal" includes any substance that is able to kill or inhibit the growth of fungi.

The term "culturing" refers to the propagation of organisms on or in various kinds of media.

"Whole broth culture" refers to a liquid culture containing both cells and media.

"Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the fungal disease states.

"Positive control" means a compound known to have fungicidal activity. "Positive controls" include, but are not limited to, commercially available chemical fungicides. Examples of commercial fungicides include dodine, fenbuconazole, and triphenyltin hydroxide. The term "negative control" means a compound known not to have fungicidal activity. Examples of negative controls are water or acetone.

The term "solvent" includes any liquid that holds another substance in solution. "Solvent extractable" refers to any compound that dissolves in a solvent and which then may be isolated from the solvent. Examples of solvents include organic solvents such as ethyl acetate.

The term "metabolite" refers to any compound, substance or byproduct of a fermentation of a microorganism that has fungicidal activity. In case of some bacteria, its growth phase can be bifurcated into a primary metabolic phase and a secondary metabolic phase. The secondary phase metabolites are metabolites that are produced after bacterial active stage growth.

A "composition" is intended to mean a combination of active agent and another compound or composition, inert (for example, a detectable agent or label) or active, such as an adjuvant.

"Phytopathogen" is a term for any organism that is pathogenic to a plant. The term "phytotoxic" is a term for any substance that inhibits plant growth or is poisonous to plants.

"Antimycotic" is a term for any agent that destroys or prevents the growth of fungi.

"Young pecan leaves" is a term describing a leave that is "½ to ¾ expanded". "Mature pecan leaves" is a term to describe a pecan leaf that is full expanded. Identification of either young pecan leaves or mature pecan leaves can be ascertained by a person having ordinary skill in the art.

"Sonicate" is a term that means disrupting biological material (such as spores) by exposure to high-frequency sound waves.

"Sporulating" is a term that means to produce or release spores.

"Hemolymph" is a term that means a fluid in the body cavities and tissues of invertebrates, in arthropods functioning as blood and in some other invertebrates functioning as lymph.

Phytopathogen Cultures

All phytopathogens were isolated from pecan and peach trees on the USDA-ARS research station in Byron, Ga., United States. The pathogens *Glomerella cingulata, Phomopsis* spp., *Monilinia fructicola*, and *Fusicladosporium effusum* were maintained on commercially prepared potato dextrose agar. *P. cactorum* was maintained on V8 juice agar media (per liter: 20 grams Bacto agar, 326 ml V-8 juice, and 3 grams calcium carbonate). The cultures were grown under light at 22-24° C. and transferred approximately every 14 days as needed.

Extraction of Bacterial Metabolites

The bacterial metabolites were isolates from various species as detailed below.

Batch 1

The bacteria *P. luminescens* (Hb), *X. bovienii* (SN), *X. nematophila* (All), and *Xenorhabdus* sp. (355) were isolated in parallel from their nematode symbionts *Heterorhabditis bacteriophora* Poinar (Hb strain), *Steinernema feltiae* (Filipjev) (SN strain), *Steinernema carpocapsae* (Weiser) (All strain), and *Steinernema riobrave* Cabanillas, Poinar & Raulson (355 strain), respectively.

Batch 2

*P. luminescens* (Hb), *P. luminescens* (VS), *Photorhabdus* sp. (MX4), *X. bovienii* (SN), and *Xenorhabdus* sp. (3-8b) were isolated from *H. bacteriophora* (Hb strain), *H. bacteriophora* (VS strain), *Heterorhabditis mexicana* Nguyen et al. (MX4 strain), *S. feltiae* (SN strain), and *S. riobrave* (3-8b strain), respectively.

The nematodes were cultured in last instar *Galleria mellonella* (L.) according to the protocol as disclosed by L. A. Lacey, edition, *Manual of Techniques in Insect Pathology* 281-324:1997 (Academic Press, San Diego, Calif.), and incorporated herein by reference. Bacterial colonies were established on nutrient agar by streaking hemolymph from insects previously infected with nematodes. *Photorhabdus* spp. and *Xenorhabdus* spp. occur in either primary or secondary phase variants. It is principally the primary phase that produces antibiotics. For primary phase bacteria selection, Tergitol-7-agar was used to indicate primary variant characteristics during bacterial isolation and culturing. The color of bacterial colonies on Tergitol-7-agar indicates phase via color. Specifically, secondary phase colonies appear red whereas primary phase colonies appear blue or green.

The composition of Tergitol-7 is as follows:

| | |
|---|---|
| Agar | 15 gm/L |
| Bromothymol Blue | 0.025 gm/L |
| Lactose | 10 gm/L |
| Peptone | 5 gm/L |
| Sodium Heptadecyl Sulfate | 0.1 gm/L |
| Yeast Extract | 3 gm/L |

Soluble organic metabolites were then extracted from the bacterial cultures following the protocol as disclosed in K. K. Ng, et al. (1997), *Canadian Journal of Plant Pathology,* 19: 125-132, and incorporated by reference herein.

Bacteria cultures were scaled up for metabolite isolation through liquid culture in Tryptic Soy Broth (Difco, Detroit, Mich.) and 0.5% yeast extract. A loopful of bacteria (approximately 4 mm area) was added to 50 ml of fresh TSY in a 300-ml Erlenmeyer flask and placed on a rotary incubator shaker at 25° C. and 130 rpm for 18 to 24 hours. The cultures were transferred to 900 ml TSY in 2 liters flasks and placed on a rotary shaker at 25° C. for 96 hours. The cells and broth were centrifuged at 10,000 rpm for 20 minutes. The supernatants containing active metabolites were extracted three times with ethyl acetate in a separatory funnel. The organic fractions containing metabolite were dried via anhydrous ammonium sulfate on a funnel, concentrated on a rotary evaporator, and dissolved in acetone. The metabolite solutions were stored at 4° C. until used as described infra., absent bacteria cells in the metabolite solution.

The composition of Tryptic Soy Broth is as follows:

| | |
|---|---|
| Pancreatic Digest of Casein | 17.0 gm/L |
| Enzymatic Digest of Soybean Meal | 3.0 gm/L |
| Sodium Chloride | 5.0 gm/L |
| Dipotassium Phosphate | 2.5 gm/L |
| Dextrose | 2.5 gm/L |

Data Analysis

Treatment effects for experiments testing in vitro antimycotic activity, suppression of *P. cactorum* on pecan leaves, and suppression of *F. effusum* on pecan shoots were determined by ANOVA; if significant treatment effect was detected (alpha=0.05) then differences were further elucidated by the Student-Newman-Keuls' test except for *P. cactorum* leaf tests in which treatment differences were separated by lsmeans. Phytotoxic effects were analyzed by comparing the rating level of each treatment that showed phytotoxicity with the control using the (non-parametric) Wilcoxon two-sample test.

The following non-limiting examples are provided to further illustrate various embodiments of the present invention.

Example 1

Antimycotic Activity In Vitro Standardized Via Initial Cell Count

Antimycotic activity was compared to a quantity of metabolites standardized by initial cell count. Metabolites were extracted from batch one bacteria isolates as stated supra. Approximately, $3 \times 10^{12}$ bacteria cells of each strain were used in the extraction and the resulting metabolites were dissolved in 20 ml of acetone. Suppressive activity of the metabolites was determined by measuring zones of inhibition on 100 mm Petri dishes containing potato dextrose agar based on protocol as described by D. I. Shapiro-Ilan et al. (2002) *Journal of Invertebrate Pathology*, 81: 86-93, and incorporated by reference herein.

Agar surfaces were sprayed with the fungal or oomycete spores ($1 \times 10^5$ to $2 \times 10^7$ per plate) of *Glomerella cingulata, M. fructicola, Phomopsis* sp., *P. cactorum*, or *F. effusum* with an airbrush. A filter paper disc (1 cm diameter) with bacterial metabolites added (20 µl) was placed in the center. Each plate received metabolites derived from approximately $3 \times 10^9$ bacterial cells. Control plates received filter paper disks with acetone (20 µl). The treatments and control were each replicated four times. After 48 hours in the dark at 25° C., the area of the inhibition zone was calculated based on the average of two diameters measured in two perpendicular directions. Fungal or oomycete growth under the disc was included in the measurement.

As noted by comparing FIGS. 1A-E, all metabolites inhibited the growth of fungal or oomycete pathogens when the metabolites was standardized by initial cell count. In the *Glomerella cingulata* assay, *X. bovienii* (SN) and *X. nematophila* (All) metabolites caused larger zones of inhibition than *X.* sp. (355) and *P. luminescens* (Hb). See FIG. 1A. The bacterial metabolites caused similar levels of inhibition in *M. fructicola* except for *X* sp., which caused less suppression than the others. See FIG. 1B. Antimycotic effects versus *Phomopsis* sp. were greatest in *X. bovienii* (SN) metabolites followed by *X. nematophila* (All). See FIG. 1C. Metabolites of *X. bovienii* (SN) and *P. luminescens* (Hb) caused the greatest suppression in *P. cactorum* whereas *X.* sp. (355) caused the least with *X. nematophila* being intermediate. See FIG. 1D. In the *F. effusum* assay, *X. bovienii* (SN) metabolites caused the greatest inhibition followed by *X. nematophila* (All) and *P. luminescens* (Hb) with X sp. (355) causing the least. See FIG. 1E.

Example 2

Antimycotic Activity In Vitro Standardized Via Concentration

Bacterial metabolites were also standardized based on concentration to compare antimycotic activity. Metabolites were extracted from both bacteria metabolite examples as stated supra. *P. luminescens* (Hb) and *X. bovienii* (SN) were included to facilitate qualitative comparison between assays standardized based on cell count versus weight of metabolite. Approximately, $7 \times 10^{12}$ bacterial cells of each strain were used in the extraction and the resulting metabolites were brought to a concentration of 50 mg per ml. Suppressive activity of the metabolites was determined by measuring zones of inhibition on potato dextrose agar plates as described supra. In these assays, 2 mg of metabolite was suspended in 40 µl (50 mg per ml) of acetone and was added to the filter paper in each Petri dish. Each treatment and control was replicated three times.

Figure 2A:
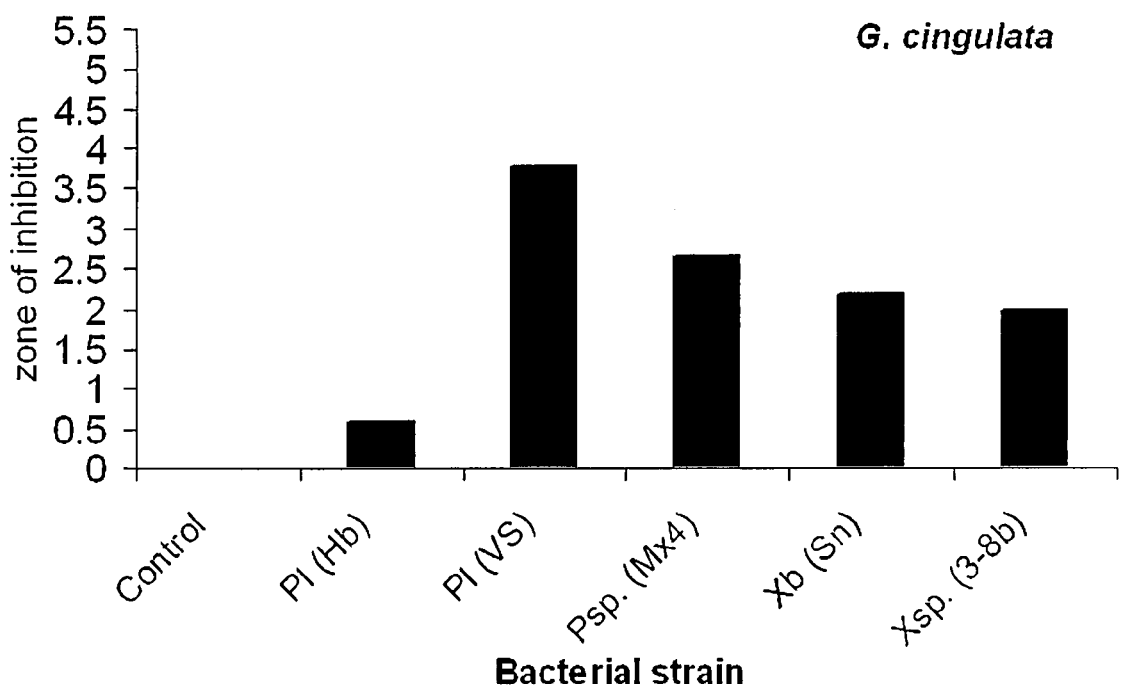
Figure 2B:
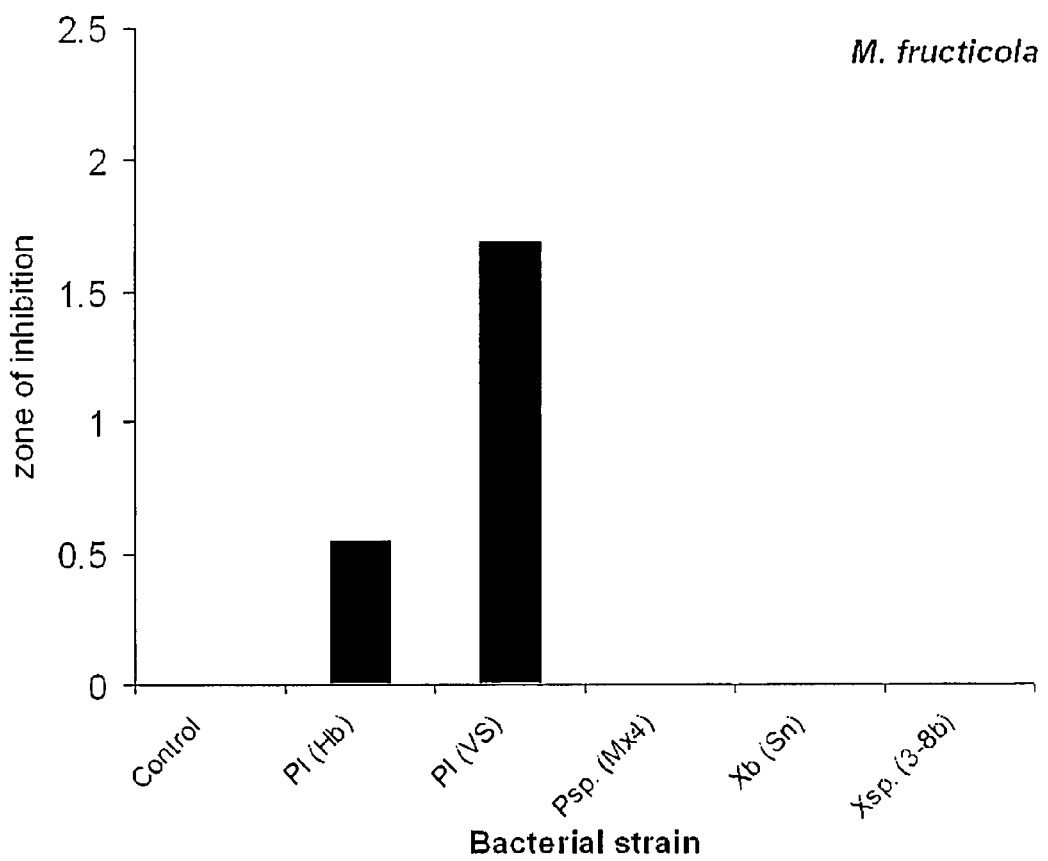
Figure 2C:
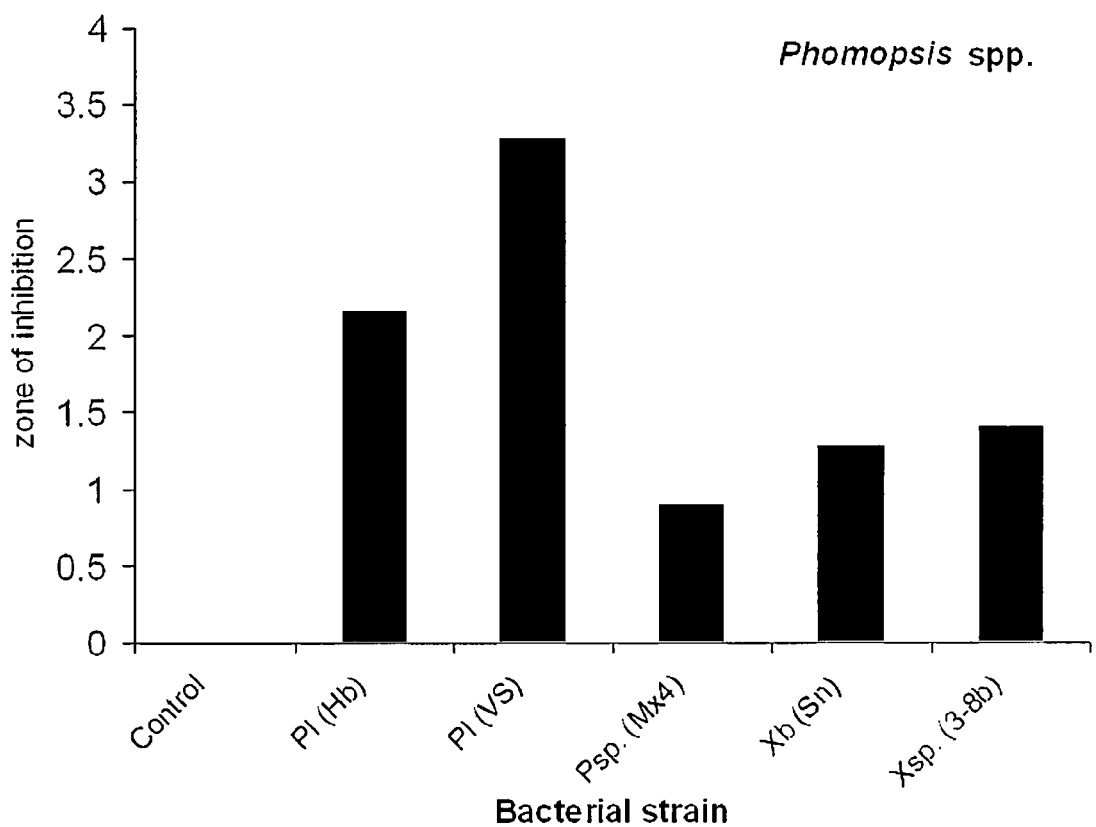
Figure 2D:
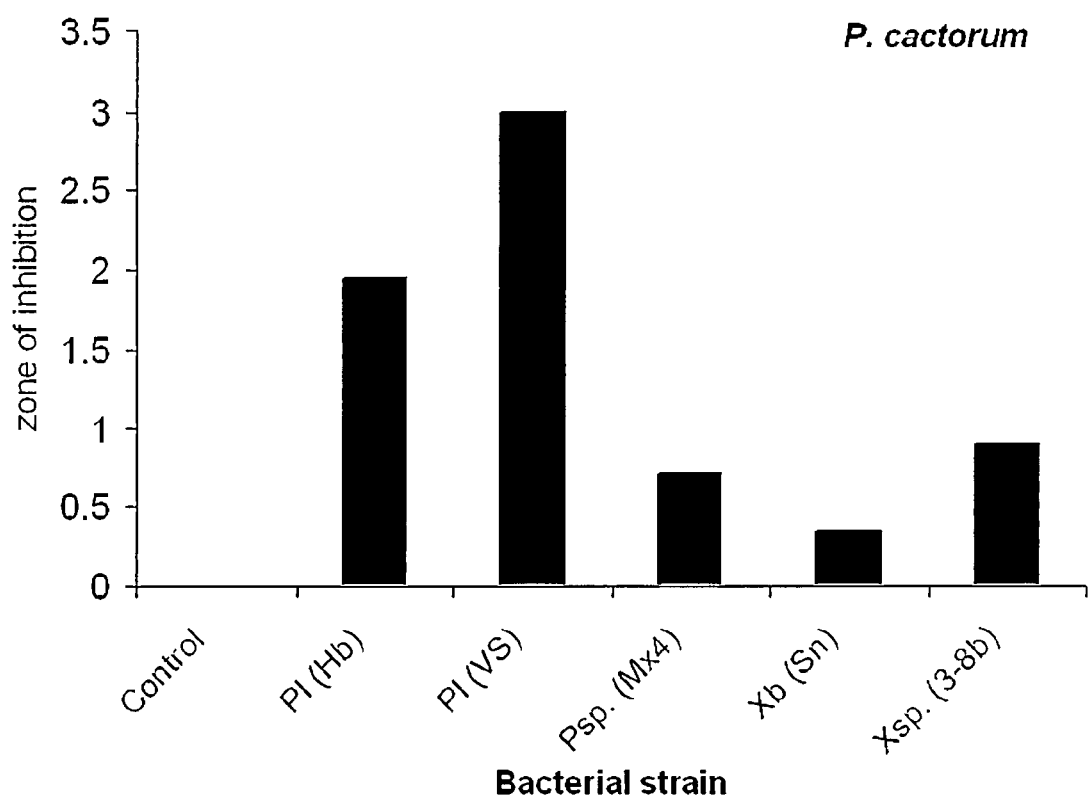
Figure 2E:
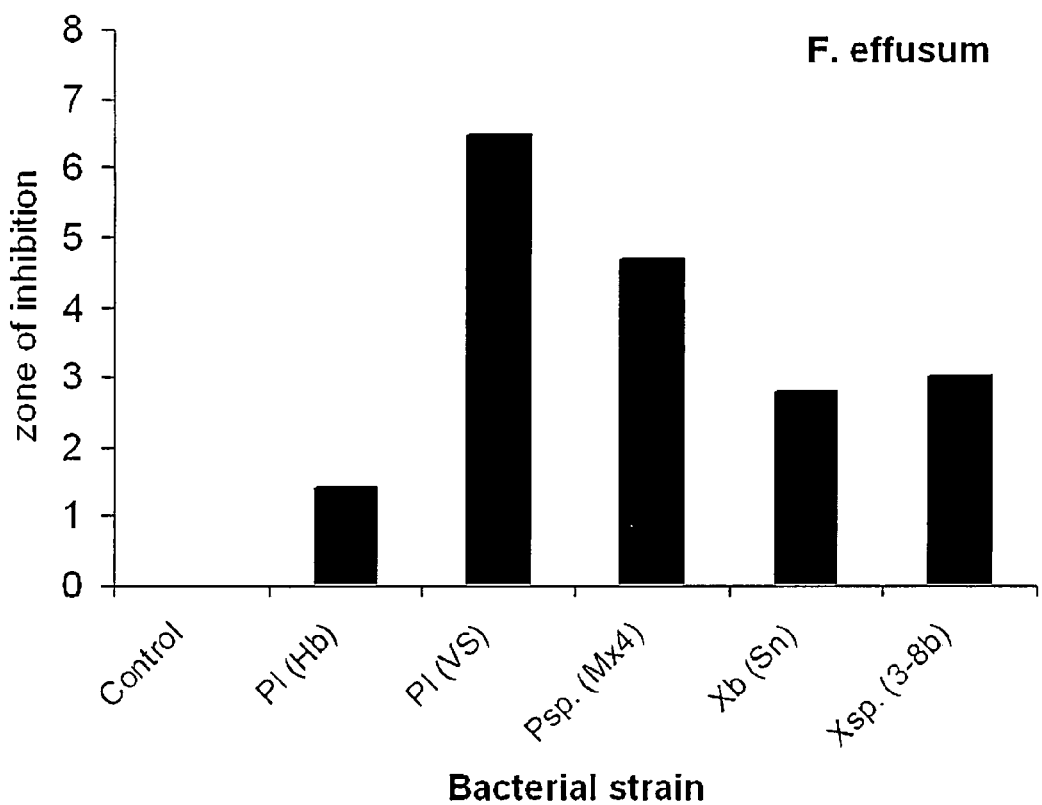

Prior to standardizing by concentration, total yields of metabolites (from $7 \times 10^{12}$ cells) were recorded as 1.25, 1.8, 2.0, 1.97, and 1.6 grams for *P. luminescens* (Hb), *P. luminescens* (VS), *Xenorhabdus* sp. (3-8b), *X. bovienii* (SN), and *Photorhabdus* sp. (MX4), respectively. In the antimycotic assays using batch metabolites, no interaction between trial and metabolite treatment was detected so the data from both trials were combined. At a standard concentration of 50 mg per ml, all metabolites inhibited the growth of *Glomerella cingulata* relative to the control except those from *P. luminescens* (Hb); there were no differences among the other metabolites. See FIG. 2A. In the *M. fructicola* assay, only *P. luminescens* (VS) metabolites caused inhibition. See FIG. 2B. Metabolites extracted from *P. luminescens* (VS) and *P. luminescens* (Hb) caused inhibition of *Phomopsis* sp. and *P. cactorum* growth whereas the other metabolites did not. See FIG. 2C and FIG. 2D. With the exception of *P. luminescens* (Hb), all metabolites caused suppression of *F. effusum* with *P. luminescens* (VS) causing the greatest inhibition followed by *Photorhabdus* sp. (MX4). See FIG. 2E.

Example 3

Phytotoxicity Tests and Suppression of *P. Cactorum* on Pecan Leaves

Suppression of *Phytophthora cactorum* on detached pecan leaves was addressed based in part by procedures described by K. K. Ng, et al., (1997) *Canadian Journal of Plant Pathology*, 19: 125-132, and incorporated by reference herein. The metabolites used in these assays were derived from bacteria isolates that were standardized based on initial cell count and dissolved in 20 ml acetone as described supra (example one). Treatments included 1%, 6%, and 12% dilutions of the original concentrations plus a distilled water and acetone control. Agar plugs of *P. cactorum* were placed on young pecan leaves of a Stuart variety previously been sprayed with 200 μl of the treatment or control by air brush and allowed to dry. The leaves were placed on 1% water agar plates and incubated at 25° C. for two days. The *P. cactorum* infection and phytotoxicity of metabolites were then assessed.

*P. cactorum* infection was determined by measuring the average maximum length of each lesion across two perpendicular directions. Phytotoxicity was measured using a rating scale where 0=none, no sign of phytotoxicity, 1=slight, very small necrotic spots on leaves indicating minimal phytotoxicity, 3=moderate, small necrotic lesions on leaves plus evidence of phytotoxicity in one or more leaf vein, and 4=severe, large necrotic lesions on leaves covering more than 20% of the surface. There were three replicates (leaves) of each treatment.

An additional test for phytotoxicity and was subsequently conducted on mature pecan leaves and mature seedling peach leaves using procedures described above (P. cactorum infection was not assessed in these latter assays); these subsequent assays included 25% dilutions as well as the 1%, 6%, and 12% dilutions.

Figure 4A:
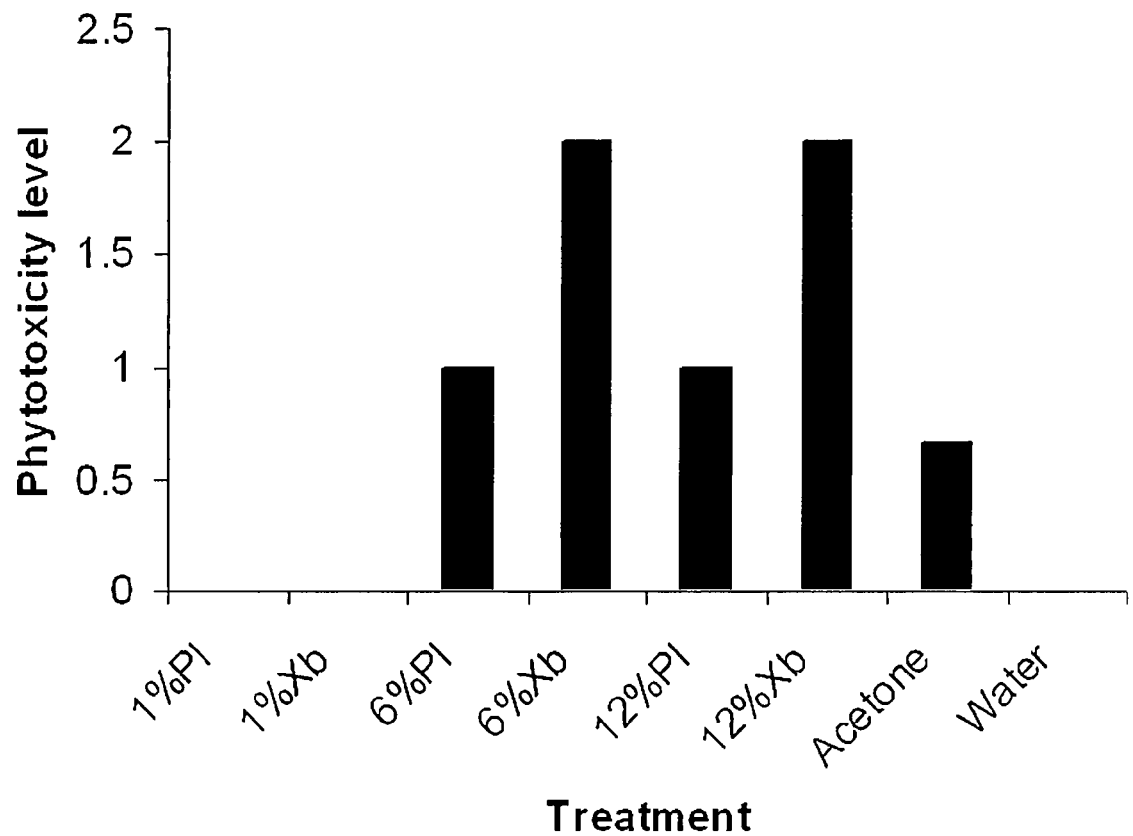

Leaves were sprayed with water or acetone controls, or metabolites from *Photorhabdus luminescens* Hb strain (Pl) or *Xenorhabdus bovienii* SN strain (Xb). Visual determination of phytotoxic level was conducted by one having skill in the art. No sign of phytotoxicity was designated as None. Very small necrotic spots on leaves indicating miminal phytoxicity was designated as Slight. Small necrotic lesions on leaves plus evidence of phytotoxicity in one or more leaf vein was designated as Moderate. In young pecan leaves, the 6% and 12% *P. luminescens* (Hb) and *X. bovienii* (SN) metabolites caused phytotoxic effects whereas the 1% dilutions did not (ratings were 0 —no phytotoxicity observed). Metabolites of *P. luminescens* (Hb) were slightly phytotoxic (average rating of 1.0) whereas *X. bovienii* (SN) was moderately phytotoxic (average rating of 2.0); these levels of phytotoxicity were all significantly greater than the water-only control, but only the *X. bovienii* (SN) metabolites caused significantly more phytotoxic effects than acetone alone. See FIG. 4A and Table 1.

TABLE 1

Bacterial Metabolite Phytotoxicity on Young Pecan Leaves

| Treatment | Rep I | Rep II | Rep III |
|---|---|---|---|
| Water | None | None | None |
| Acetone | None | Slight | Slight |
| 1% Pl | None | None | None |
| 6% Pl | Slight | Slight | Slight |
| 12% Pl | Slight | Slight | Slight |
| 1% Xb | None | None | None |
| 6% Xb | Moderate | Moderate | Moderate |
| 12% Xb | Moderate | Moderate | Moderate |

Figure 4B:
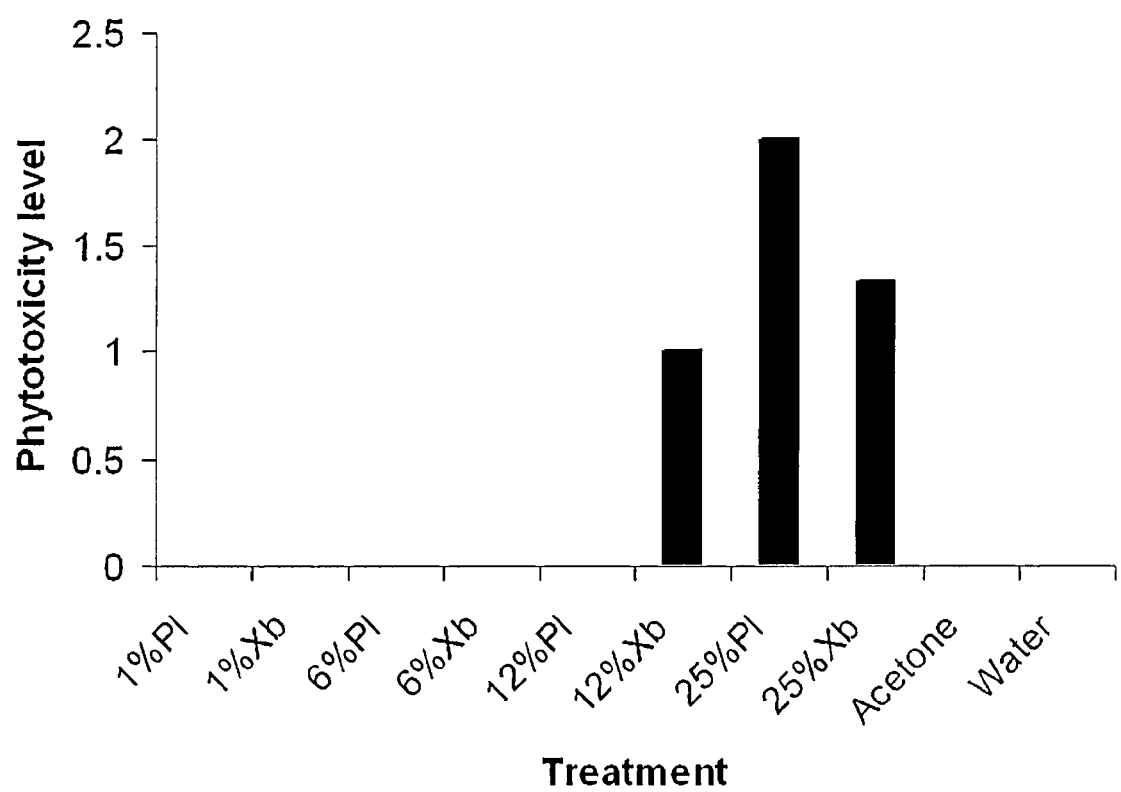

In mature pecan leaves, 25% *P. luminescens* (Hb) and 12% or 25% *X. bovienii* (SN) caused phytotoxic effects whereas lower dilutions of the metabolites did not. See FIG. 4B and Table 2. Leaves were sprayed with water or acetone controls, or metabolites from *Photorhabdus luminescens* Hb strain (Pl) or *Xenorhabdus bovienii* SN strain (Xb). Visual determination of phytotoxic level was conducted by one having skill in the art. No sign of phytotoxicity was designated as None. Very small necrotic spots on leaves indicating miminal phytoxicity was designated as Slight. Small necrotic lesions on leaves plus evidence of phytotoxicity in one or more leaf vein was designated as Moderate. The 12% and 25% *X. bovienii* (SN) treatments caused slight phytotoxicity ratings of 1.0 and 1.3, respectively. The 25% *P. luminescens* (Hb) treatment caused moderate phytotoxicity rating of 2.0. All of these phytotoxicity ratings were significantly greater than the acetone and water controls, which had a zero rating. None of the metabolite dilutions (1 to 25%) of *P. luminescens* (Hb) and *X. bovienii* (SN) metabolites caused any observable phytotoxicity in peach leaves.

TABLE 2

Bacterial Metabolite Phytotoxicity on Mature Pecan Leaves[1].

| Treatment | Rep I | Rep II | Rep III |
|---|---|---|---|
| Water | None | None | None |
| acetone | None | None | None |
| 1% Hb | None | None | None |
| 6% Hb | None | None | None |
| 12% Hb | None | None | None |
| 25% Hb | Moderate | Moderate | Moderate |
| 1% Sf | None | None | None |
| 6% Sf | None | None | None |
| 12% Sf | Slight | Slight | Slight |
| 25% Sf | Slight | Slight | Moderate |

Figure 5:
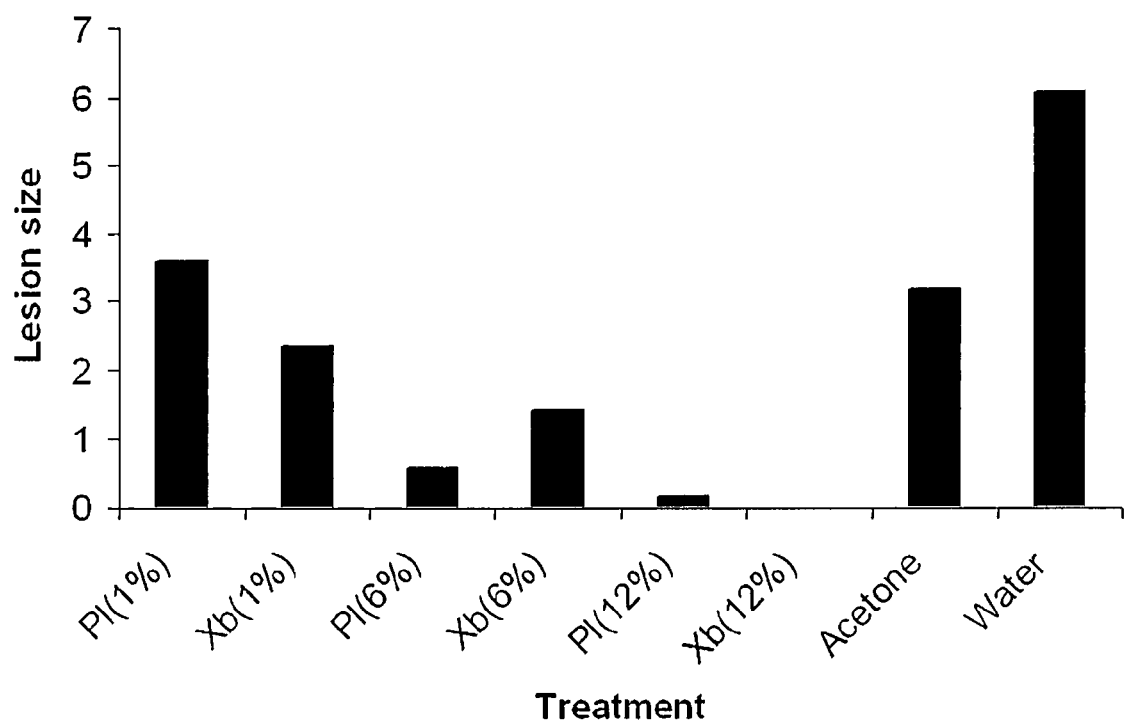
Figure 6A:
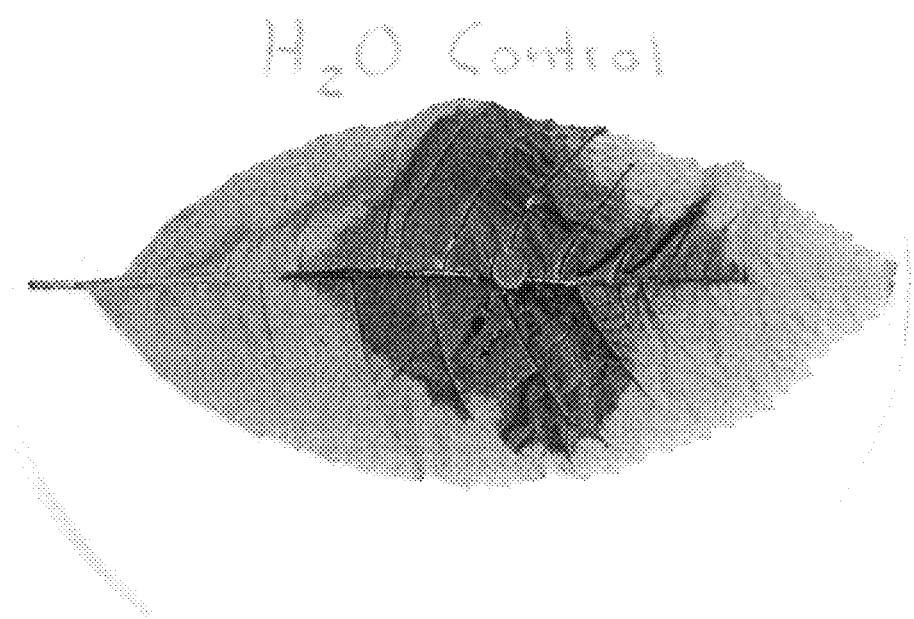
Figure 6B:
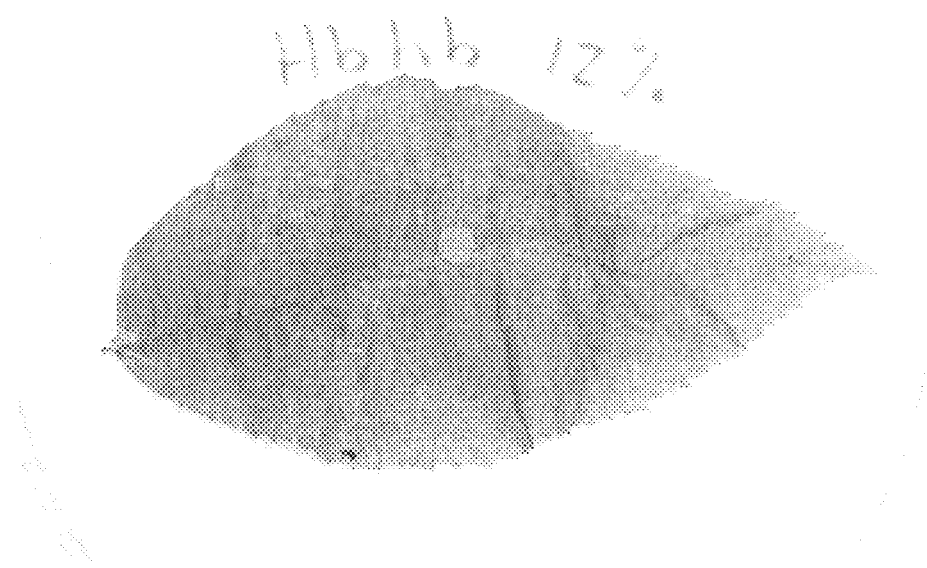

Metabolites of *P. luminescens* (Hb) diluted to 6% or 12% and *X. bovienii* diluted to 12% caused reductions in the size of *P. cactorum* lesions; lower concentrations of the metabolites did not suppress lesion growth. See FIG. 5. The level of suppression (control) based on Abbott's formula relative to the acetone control was 82%, 94%, and 100% for the 6%, 12% *P. luminescens* (Hb) and 12% and *X. bovienii* treatments, respectively.

Example 4

Suppression of *F. effusum* on Pecan Terminal Shoots

Dormant twigs with spore lesion constitute a primary source of scab infestation in pecan orchards. Scab disbursal via twig lesion sporulation occurs in early spring when temperatures are optimal. Terminal shoots exhibiting *F. effusum* lesions were collected from pecan orchards of the Witchita variety at USDA-ARS orchards in Byron, Ga. The shoots were selected for uniformity in diameter, cut into 5 cm segments, and placed into 1.5×10 cm test tubes.

Terminal Shoot Sonication and Spore Count

Pecan shoots were sonicated for 30 minutes in 6 ml of 1% TWEEN 20 solution (polyoxyehtylene (20) sorbitan monolaurate). The number of spores released per lesion was counted via a hemocytometer. Shoot lesions were designated as the baseline treatment. A portion of the shoots were sonicated and counted prior to exposure to fungicidal treatments to verify that the shoots had not sporulated. The initial shoots lesions were designated as the baseline treatment.

Shoots were exposed to the following fungicidal treatments: undiluted metabolites derived from either *P. luminescens* (Hb) or *X. bovienii* (SN), and three chemical fungicide products used for control of *F. effusum*, i.e., dodine (Dodine 65W, 65% active ingredient, wettable powder, Platte Chemical Co. Greeley, Colo.), fenbuconazole (ENABLE 2F, 240 grams/liter active ingredient, flowable, Dow AgroSciences, Indianapolis Ind.), and triphenyltin hydroxide (SUPERTIN, 80% active ingredient, wettable powder, Griffin L. L. C., Valdosta, Ga.). The bacteria *P. luminescens* (Hb) was isolated from *Heterorhabditis bacteriophora* Poinar. The bacteria *X. bovienii* (SN) was isolated from *Steinernema feltiae* (Filipjev).

The shoots were also exposed to a water control and acetone control. Acetone was used as a solvent for the metabolites. The treatments were applied using an airbrush sprayer. The shoots were incubated at 25° C. for 72 hours, and exposed to sonification and quantification of spores. Ten replicate shoots for each treatment and the experiment was repeated once.

Figure 3:
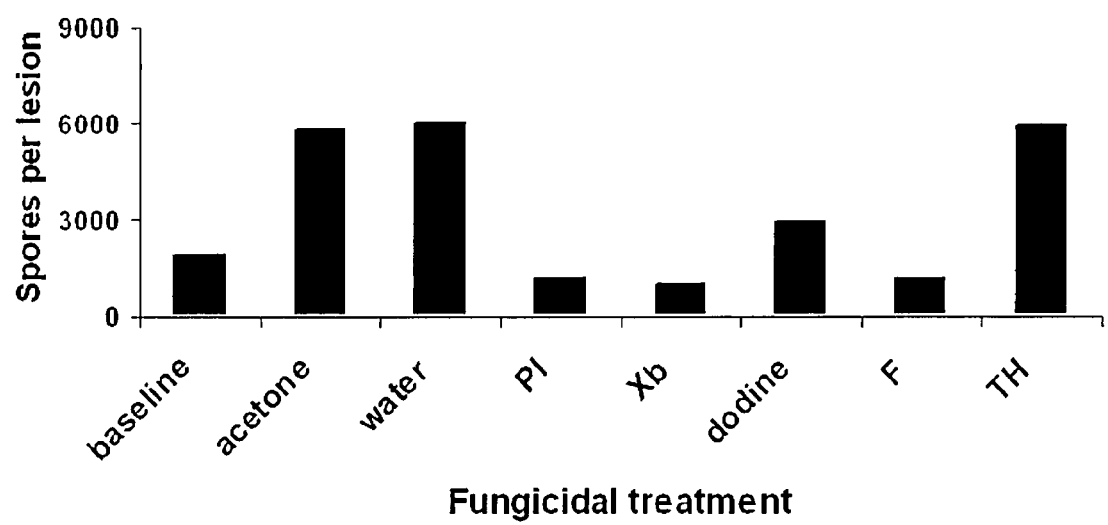

No interaction between trial and metabolite treatment was detected in the suppression of *F. effusum* on pecan shoot experiment, and the data from both trials were combined. Relative to the acetone or water control, applications of *P. luminescens* (Hb) and *X. bovienii* (SN) metabolites as well as chemical fungicides dodine and fenbuconazole fungicides suppressed sporulation of *F. effusum* on pecan shoots. No effect was detected in triphenyltin hydroxide applications. See FIG. 3. Based on Abbott's formula and relative to the acetone control, *P. luminescens* (Hb) and *X. bovienii* (SN) metabolites as well as chemical fungicides dodine and fenbuconazole treatments caused 80.4%, 83.7%, 49.6%, and 80.4% suppression of *F. effusum* sporulation.

In vitro assays indicated that growth of all fungal or oomycete pathogens of pecan and peach tested were suppressed by metabolites from *Photorhabdus* spp. and *Xenorhabdus* spp. At 6% and 12% dilutions, metabolites from *P. luminescens* (Hb) and *X bovienii* (SN) produced 90 to 100% suppression of *P. cactorum* lesions in pecan leaves with only slight or moderate phytotoxicity. No phytotoxicity was observed on peach leaves.

While the invention has been described with reference to details of the illustrated embodiment, these details are not intended to limit the scope of the invention as defined in the appended claims.

The embodiment of the invention in which exclusive property or privilege is claimed is defined as follows:

1. A method of controlling a fungal pathogen consisting essentially of culturing strain *Xenorhabdus bovienii* SN, NRRL B-50010, or strain *Photorhabdus luminescens* VS, NRRL B-50007, in a nutrient culture medium and under conditions effective for the production of antifungal metabolites, extracting the antifungal metabolites from the culture, and contacting the extracted antifungal metabolites with a fungal pathogen of the group consisting of *Glomerella cingulata, Phomopsis, Phytophthora cactorum*, and *Fusicladosporium effusum*, wherein the extracted antifungal metabolites inhibit the growth of the fungal pathogen on a plant selected from the group consisting of *Carya illinoensis* and *Prunus persica*.

2. The method as recited in claim 1 wherein the extracted antifungal metabolites are extracted from a culture supernatant or a filtrate.

3. The method as recited in claim 1 wherein the extracted antifungal metabolites are contacted with the plant *Carya illinoensis*.

4. The method as recited in claim 1 wherein the extracted antifungal metabolites are contacted with the plant *Prunus persica*.

5. The method as recited in claim 1 wherein the extracted antifungal metabolites are contacted with the whole plant, the seed of the plant or the locus of the plant, wherein the locus of the plant is soil or any other plant growth medium.

\* \* \* \* \*